United States Patent
Brockwell et al.

(10) Patent No.: US 6,492,548 B1
(45) Date of Patent: Dec. 10, 2002

(54) PROCESS FOR THE OXIDATION OF ALKANES

(75) Inventors: Jonathan L Brockwell, South Charleston, WV (US); Mark A Young, South Charleston, WV (US); William G Etzkorn, Hurricane, WV (US); Barbara K Warren, Charleston, WV (US); John M Maher, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 2 days.

(21) Appl. No.: 09/665,098

(22) Filed: Sep. 20, 2000

Related U.S. Application Data

(63) Continuation of application No. 09/155,808, filed as application No. PCT/US97/05054 on Mar. 27, 1997, now abandoned.
(60) Provisional application No. 60/014,679, filed on Apr. 1, 1996.

(51) Int. Cl.[7] .......................... C07C 51/16; C07C 27/10; C07C 53/06; C07C 51/235
(52) U.S. Cl. ..................... 562/545; 562/512.2; 562/532
(58) Field of Search ................................. 562/532, 531, 562/523, 545, 521

(56) References Cited

U.S. PATENT DOCUMENTS

| 3,293,290 A | * 12/1966 | Flint et al. ................... 260/533 |
| 4,260,822 A | 4/1981 | Krieger et al. ............... 562/549 |
| 4,413,147 A | 11/1983 | Khoobiar ..................... 568/476 |
| 4,532,365 A | 7/1985 | Khoobiar ..................... 568/479 |
| 4,999,452 A | 3/1991 | Bunning et al. ............. 560/208 |
| 5,077,434 A | 12/1991 | Sarumaru et al. ........... 562/534 |
| 5,155,262 A | 10/1992 | Etzkorn et al. ............. 562/532 |
| 5,183,936 A | 2/1993 | Etzkorn et al. ............. 562/532 |
| 5,198,578 A | 3/1993 | Etzkorn et al. ............. 562/532 |
| 5,218,146 A | 6/1993 | Takata et al. ................ 562/535 |
| 5,243,082 A | 9/1993 | Etzkorn et al. ............. 568/465 |
| 5,321,180 A | 6/1994 | Davis .......................... 585/431 |
| 5,354,915 A | 10/1994 | Reichle ....................... 568/881 |
| 5,696,282 A | 12/1997 | Shaw et al. .................. 560/152 |
| 5,705,684 A | 1/1998 | Hefner et al. ............... 562/545 |

FOREIGN PATENT DOCUMENTS

| EP | 0117146 | 8/1984 |
| GB | 2118939 | 11/1993 |

* cited by examiner

Primary Examiner—Mukund J. Shah
Assistant Examiner—Zachary C. Tucker

(57) ABSTRACT

Processes are disclosed for the oxidation of alkanes such as, for example, propane, to form unsaturated carboxylic aldehydes and acids such as, for example, acrolein and acrylic acid. The processes utilize oxygen and recycle alkanes, e.g. propane, to the aldehyde reactor. The presence of the alkane-to-aldehyde reaction can enhance the efficiency of the processes.

13 Claims, 1 Drawing Sheet

Continuous Process for Conversion of Propane to Acrolein or Acrylic Acid

Continuous Process for Conversion of Propane to Acrolein or Acrylic Acid

PROCESS FOR THE OXIDATION OF ALKANES

This application is a continuation of U.S. Ser. No. 09/155,808, now abandoned filed Oct. 1, 1998 based on international application number PCT/US/97/05054, filed Mar. 27, 1997, which claims benefit of Provisional Application No. 60/014,679, filed Apr. 1, 1996.

FIELD OF THE INVENTION

This invention relates to the oxidation of alkanes such as, for example, propane, to form unsaturated, carboxylic aldehydes and acids such as, for example, acrolein and acrylic acid.

BACKGROUND OF THE INVENTION

Processes for producing acrylic acid by vapor phase catalytic oxidation of propylene using molecular oxygen are known and used on an industrial scale.

One of the typical processes for industrial production of acrylic acid is as follows. Propylene is converted mainly into acrolein and a small amount of acrylic acid in a first reaction step by supplying a mixture of propylene, air and steam to produce the acrolein. The acrolein product is supplied to a second reactor without separation of products for the subsequent reaction of acrolein to form acrylic acid. Additional air and steam for the second step are supplied as required.

In another typical process, the product gas containing acrylic acid obtained from the second reactor is introduced into a collecting apparatus to obtain acrylic acid as an aqueous solution and a part of remaining waste gas containing unreacted propylene from the collecting apparatus is recycled to the first reactor inlet together with the starting gas mixture of propylene, air and steam.

Various improvements to the above-mentioned processes have been proposed to produce acrylic acid efficiently by vapor phase catalytic oxidation of propylene. Many such improvements have been directed to the use of certain catalysts. Examples of catalysts used for industrial production are Mo—Bi composite oxide catalysts for the first step, i.e., acrolein production, and Mo—V composite oxide catalysts for the second step, i.e., acrylic acid production. There are many reasons why the characteristics of these oxidation catalysts affect the economy of the processes. Primarily, the selectivity of the catalysts for the reactions affects the quantity of propylene used, and the catalyst activity in the reactions affects the space time yield of acrylic acid.

Further enhancements directed to the use of propane as a feed source are desired because propane is more readily available and less expensive than propylene. It would be desireable if the propane could be simultaneoulsy utilized to enhance the reaction efficiency of the processes in addition to being a feed source.

SUMMARY OF THE INVENTION

By the present invention, improved continuous processes are provided for the conversion of alkanes such as, for example, propane, to unsaturated aldehydes such as, for example, acrolein, and acids such as, for example, acrylic acid.

In the processes of the present invention, an alkane having from about 2 to 8 carbon atoms per molecule, e.g., propane, is first converted to an alkene having the same number of carbon atoms as the alkane, e.g., propylene, and then alkene is converted to an unsaturated aldehyde having the same number of carbon atoms as the alkene, e.g., acrolein. The aldehyde is then converted to an unsaturated carboxylic acid having the same number of carbon atoms as the aldehyde, e.g., acrylic acid.

By operating at low propane-to-propylene conversion in accordance with the present invention, the selectivity to propylene can be made unexpectedly high, e.g., between 80 and 100 mole %. Since the presence of propane has been found to enhance the efficiency of the propylene-to-acrolein reaction, the low propane conversion is not detrimental to the process. Indeed, even though the feed to the acrolein reactor may contain propylene in low concentrations, e.g., 5 to 20 mole %, the low-conversion, high-selectivity mode of operation can be highly efficient provided unreacted propane is recycled to the propane oxidation reactor. Recycle operation is particularly feasible in accordance with the present invention because oxydehydrogenation catalysts, which are preferred for use in the present invention, are substantially unaffected by species such as carbon oxides and water which are formed in the acrolein reactor. Hence, after recovery of the acrolein, the noncondensed gases containing propane may be recycled without significant, additional purification steps.

DETAILED DESCRIPTION OF THE INVENTION

Figure 2:
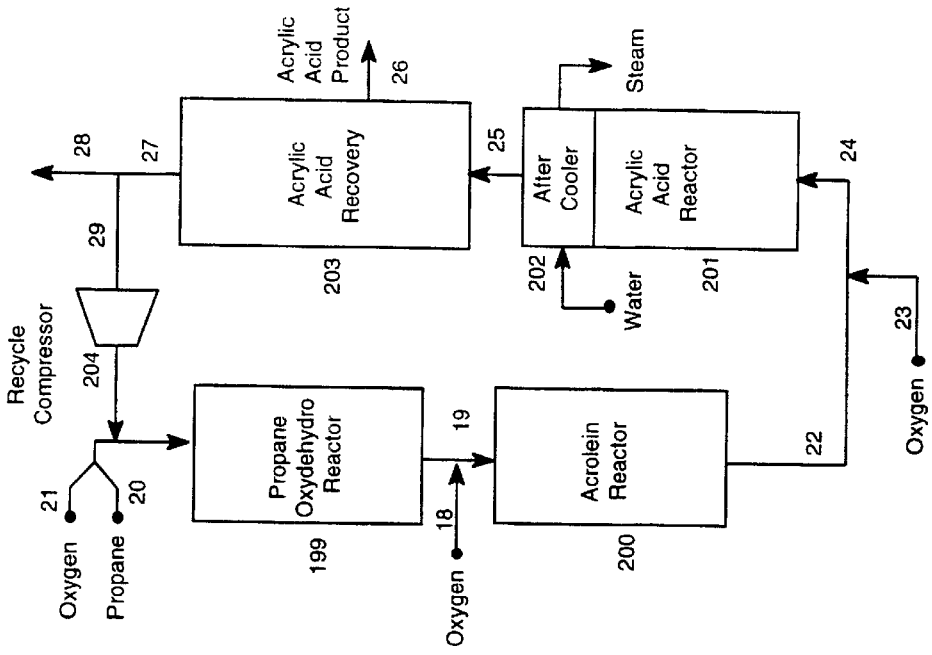
FIG. 2 is a simplified process flow diagram of a process for converting propane to acrylic acid in accordance with the present invention.

In the present invention, as the starting material alkane it is preferred to employ a $C_{2-8}$ alkane, preferably a $C_{3-5}$ alkane, and more preferably propane, isobutane or n-butane. As the starting material, propane or isobutane is most preferred. According to the processes of the present invention, from such an alkane, an unsaturated carboxylic acid such as an alpha, beta -unsaturated carboxylic acid can be obtained. For example, when propane or isobutane is used as the starting material alkane, acrylic acid or methacrylic acid can be obtained, respectively.

The purity of the starting material alkane is not particularly limited, and an alkane containing a lower alkane such as methane, air or carbon dioxide, as impurities, may be used. Further, the starting material alkane may be a mixture of various alkanes. Typically, the feed will comprise at least 30 mole percent, preferably at least 50 mole percent and more preferably at least 80 mole percent propane. The source of the alkane, e.g., propane feed, for use in the process of the present invention is not critical.

Although the invention is mainly hereinafter described with reference to propane, acrolein and acrylic acid, those skilled in the art will recognize that the present invention is also applicable to butane, methacrolein and methacrylic acid and other hydrocarbons e.g., ethane or pentane.

The oxygen source for use in the processes of the present invention (both for propane oxidation and propylene oxidation) is not critical. However, the use of air is not preferred because the nitrogen content can adversely affect the ability to recycle effluent gases. Preferably, the oxygen source comprises at least 90 mole percent and more preferably at least 95 mole percent oxygen. The ratio of propane to oxygen varies with the desired conversion and the selectivity of the catalyst, but generally is in the range of 5/1–40/1. The reaction can also be conducted in the presence of diluents such as, for example, steam. Such diluents, when employed, can be fed at 0–50 times the partial pressure of the propane, with 0.2–10 times being usual.

In the propane-to-propylene reaction, it is preferred to employ a starting material gas which contains steam. In such a case, as a starting material gas to be supplied to the propane reactor, a gas mixture comprising steam-containing propane and an oxygen-containing gas, is usually used. However, the steam-containing propane and the oxygen-containing gas may be alternately supplied to the reaction system. The steam to be employed may be present in the form of steam gas in the reaction system, and the manner of its introduction is not particularly limited. However, steam is not essential in the process of the present invention.

Any catalyst effective for the conversion of propane to propylene is suitable for use in the present invention. Preferred catalysts include, for example, oxydehydrogenation catalysts which comprise promoted MoVNb oxides, vanadyl pyrophosphate and other oxydehydrogenation catalysts. Such catalysts and others suitable for the oxidation of propane are described, for example, in U.S. Pat Nos. 4,148,757, 4,212,766, 4,260,822 and 5,198,580 and by E. M. Thorsteinson, T. P. Wilson, F. G. Young, and P. H. Kasai, J. Catal., 52, 116 (1978).

An example of a suitable catalyst for use in accordance with the present invention is a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$$0.25 < rMo < 0.98$$

$$0.003 < rV < 0.5$$

$$0.003 < rTe < 0.5$$

$$0.003 < rX < 0.5$$

wherein r Mo, r V, r Te and r X are molar fractions of Mo, V, Te and X, respectively, based on the total amount of the essential components exclusive of oxygen. This catalyst is further described in U.S. Pat. No. 5,380,933.

For the propane oxidation, the reaction temperature is usually from about 200 to 550° C., preferably from about 250 to 450° C., more preferably from about 350 to 440° C. The gas hourly space velocity in the vapor-phase reaction is usually within a range of from about 100 to 10,000 $hr^{-1}$, preferably from about 300 to 6,000 $hr^{-1}$, more preferably from about 1000 to 4,000 $hr^{-1}$. As used herein, "gas hourly space velocity" means the volume of reactant gas at standard conditions (0° C. and 1 atm pressure) passed over the catalyst in one hour divided by the total volume occupied by the catalyst. Further, as a diluting gas to adjust the space velocity and the oxygen partial pressure, an inert gas such as nitrogen, argon or helium may be employed. This reaction is typically conducted at a slightly elevated pressure, e.g., 2 to 6 atm.

Any suitable reactor sequence known to those skilled in the art may be used for the propane-to-propylene reaction. For example, the reaction can be conducted in a single stage, or can be conducted in two or more stages with oxygen introduction between the stages where introduction of the entire oxygen requirement at a single point could create flammable process mixtures. Further details on the conversion of propane to propylene and suitable equipment, e.g., reactors, are known to those skilled in the art.

In the propane-to-propylene reaction, particularly in the case of the propane oxydehydrogenation reaction, the propylene selectivity decreases with increasing propane conversion. Preferably, the propane-to-propylene reaction is conducted to provide for relatively low conversions of propane with high selectivities to propylene. More specifically, it is preferred that the conversion of propane be from about 5 to 40 percent and more preferably from about 10 to 30 percent. As used herein, the term "propane conversion" means the percentage of propane fed which is reacted. It is preferred that the selectivity of the conversion of propane to propylene be from about 50 to 98 percent and more preferably from about 80 to 98 percent. As used herein, the term "propylene selectivity" means the moles of propylene produced per mole of propane reacted expressed as a percentage.

In the present invention, propylene and oxygen are reacted over a catalyst at elevated temperature to produce acrolein. Water is a co-product of the reaction. A number of by-products are formed including carbon monoxide, carbon dioxide, formaldehyde, acetaldehyde, acetic acid and acrylic acid. Neither the propylene nor the oxygen in the reactor feed is totally converted. The noncondensable components in the reaction product, e.g., oxygen, propylene, carbon monoxide, carbon dioxide, propane and other light hydrocarbons, are separated from the condensable organic compounds, compressed and preferably recycled to the reactor inlet. In this way, utilization of oxygen and propylene can be very high.

In one aspect of the present invention, the propylene-to-acrolein reaction is preferably conducted in the presence of an essentially anhydrous diluent gas such as described in U.S. Pat No. 5,198,578. The essentially anhydrous diluent gas typically comprises a mixture of nitrogen, carbon dioxide, methane, ethane and propane; however, any other essentially anhydrous inert gas can be included. Some other useful inert gases include helium, argon, hydrogen, saturated hydrocarbon gases, $N_2O$, and carbon monoxide. When water is present as a trace impurity in any of the materials introduced into the reactors, at the elevated temperature required for these reactions the water is immediately converted to steam.

In other aspects of the present invention, some steam, e.g., about 0.3 to 8 moles per moles of propylene, may be utilized in the propylene-to-acrolein reaction. In these aspects, the steam may be effective in promoting the process possibly because it facilitates the desorption of the main products of the catalytic vapor-phase oxidation of propylene, i.e., acrolein and acrylic acid, or possibly because it participates directly in the reaction.

The propylene-to-acrolein reaction is not dependent upon any particular catalyst and any catalysts effective for the conversion of propylene to acrolein may be used. Typical catalysts are molybdenum-bismuth-iron-based mixed-metal-oxide oxidation catalysts, such as, for example, those disclosed in U.S. Pat. Nos. 3,825,600, 3,649,930, 4,339,355, 5,077,434 or 5,218,146. It may also be possible to conduct both the propane-to-propylene and propylene-to-acrolein reactions in a single reactor with one or more stages.

An example of a catalyst suitable for the propylene-to-acrolein reaction is an oxide catalyst containing Mo, Fe, and Bi. This catalyst is represented by the following general formula:

$$Mo_aW_bBi_cFe_dA_eB_fC_gD_hO_x$$

wherein Mo is molybdenum, Bi is bismuth, W is tungsten, Fe is iron, O is oxygen, A is at least one element selected from the group consisting of nickel and cobalt, B is at least one element selected from the group consisting of alkali metals, alkaline earth metals, and thallium, C is at least one element selected from the group consisting of phosphorus, arsenic, boron, and niobium, and D is at least one element selected from the group consisting of silicon, aluminum, and titanium, and the subscripts a, b, c, d, e, f, g, h, and x are respectively the numbers of atoms of the elements Mo, W, Bi, Fe, A, B, C, D, and O, providing that a=2 to 10, b=0 to 10, on condition that a+b=12, c=0.1 to 10.0 d=0.1 to 10, e=2 to 20, f=0.005 to 3.0, g=0 to 4, h=0.5 to 15, and x is a number required to satisfy the valance requirements of the other elements. This catalyst is described in U.S. Pat No. 5,218,146.

The catalysts for use in the processes of the present invention may be in the form of pellets, beads, or rings containing a through hole which are produced by a tableting machine or an extruding machine or otherwise in a form having catalytic components deposited on a refractory carrier. Suitable propylene-to-acrolein catalysts are commercially available, for example, from Nippon Shokubai, Tokyo, Japan; Nippon Kayaku, Tokyo, Japan; and Mitsubishi, Tokyo, Japan.

As regards the acrolein reaction gas composition, the content of propylene is in the range of 5 to 30 volume percent, preferably 7 to 15 volume percent, that of oxygen in the range of 8 to 40 volume percent, preferably 12 to 30 volume percent, that of a saturated aliphatic hydrocarbon having 1 to 5 carbon atoms, preferably 1 to 3 carbon atoms, e.g., propane, in the range of 5 to 70 volume percent, preferably 10 to 60 volume percent, that of carbon monoxide in the range of 0 to 50 volume percent, preferably 15 to 45 volume percent, that of carbon dioxide in the range of 0 to 50 volume percent, preferably 5 to 40 volume percent, (providing that the total content of the hydrocarbon, carbon monoxide and carbon dioxide is in the range of 40 to 90 volume percent, preferably 60 to 85 volume percent), and that of steam, when present, in the range of 0 to 50 volume percent, preferably 5 to 40 volume percent, (providing that the molar ratio of steam to propylene is in the range of 0.3 to 8, preferably 0.3 to 5), the molar ratio of oxygen to propylene is in the range of 1.0 to 2.5, preferably 1.5 to 2.0, and the contact time is in the range of 0.3 to 1.5 seconds, preferably 0.5 to 1.2 seconds. The catalyst is preferably capable of effecting a conversion of propylene of not less than 70 mole percent, preferably not less than 80 mole percent.

Preferably, the concentration of propane in the feedstream to the acrolein reaction zone is from about 5 to 70 volume percent, more preferably from about 10 to 60 volume percent and most preferably from about 10 to 40 volume percent, based on the total volume of the feedstream. As used herein, the terms "mole percent" and "volume percent" are equivalent as they relate to the concentrations of components in vapor streams.

Quite surprisingly, it has been found that the propylene-toacrolein reaction efficiency can be substantially enhanced when using propane-containing feedstreams as described above. Preferably, the acrolein reaction efficiency is from about 65 to 97 percent and more preferably from about 75 to 90 percent. As used herein, the term "propylene-to-acrolein reaction efficiency" means moles acrolein produced per mole propylene fed expressed as a percentage.

Typically, approximate ranges for feed compositions are defined based on the generalized operating constraints discussed above. Propylene-to-acrolein reaction feeds in the following quantities are typically particularly useful:

Propylene: Up to about 16 g-mole per hour/liter of acrolein reaction catalyst, preferably up to about 10 g-mole per hour/liter of acrolein reaction catalyst;

Oxygen: 1.1 to 2.1:1 $O_2/C_3H_6$ ratio, such that there is up to about 33.6 g-mole per hour O2/liter of acrolein reaction catalyst, preferably up to about 21 g-mole per hour $O_2$/liter of acrolein reaction catalyst;

Diluent: About 0.7 to 16:1 inert diluent/$C_3H_6$ ratio, preferably 2 to 10:1 inert diluent/$C_3H_6$ratio.

The general reaction conditions are not narrowly critical, and are those known to the art. The propylene-to-acrolein reaction operates at temperatures of about 250 to 450° C., although temperatures of about 270 to 425° C. are preferred.

Operating pressures of about 1 to 4 atm are typical, although subatmospheric, atmospheric, or superatmospheric pressures may be used. Preferred commercial modes of operation will often minimize pressures, but pressures are typically held in the 2-to 3-atm range due to system pressure-drop constraints.

Flow rates can be varied to achieve contact times of from about 0.2 to 2 seconds in the propylene-to-acrolein reaction; however, typical commercial flows provide about 0.3 to 1.5 seconds contact time. Contact times of about 0.5 to 1.2 seconds are preferred. As used herein, "contact time" is defined as the ratio of the open volume in the catalyst bed to the process volumetric flow at process conditions.

The type of reactor used in the conversion of propylene to acrolein is not critical and may be, for example, a fixed-bed, tubular-flow reactor with liquid coolant passed through the shell. Fluidized bed reactors may also be employed. Further details of suitable reactors are known to those skilled in the art.

The catalyst for use in the acrolein-to-acrylic acid reaction can be any catalyst suitable for the conversion of acrolein to acrylic acid and may be the same or different than the catalyst used to oxidize the propane. Preferably, the acrolein oxidation catalyst is an oxide catalyst containing molybdenum and vanadium, preferably an oxide catalyst represented by the following general formula:

$$Mo_mV_nQ_qR_rS_sT_tO_y$$

wherein Mo is molybdenum, V is vanadium, Q is at least one element selected from the group consisting of tungsten and niobium, R is at least one member selected from the group consisting of iron, copper, bismuth, chromium, and atimony, S is at least one element selected from the group consisting of alkali metals and alkaline earth metals, T is at least one element selected from the group consisting of silicon, aluminum and titanium, and 0 is oxygen and the subscripts m, n, q, r, s, t, and y are respectively the numbers of atoms of the corresponding elements, providing that n=2 to 14, q=0 to 12, r=0 to 6, s=0 to 6, t=0 to 30 where m=12, and y is a number determined by the valance requirements of the other elements in the oxidation states. This type of catalyst is further described in U.S. Pat No. 5,218,146. Other catalysts for the conversion of acrolein to acrylic acid are described in U.S. Pat. Nos. 4,892,856, 5,077,434, 5,198,580 and 5,380,933 for example. Suitable acrolein-to-acrylic acid catalysts are commercially available, for example, from Nippon Shokubai, Tokyo, Japan.

As regards the conditions for the acrolein oxidation, the reaction temperature is typically in the range of about 180°

C. to 350° C., preferably about 200° C. to 320° C., and the contact time is in the range of about 1.0 to 7.2 seconds, preferably about 1.6 to 6.0 seconds.

Preferably, in accordance with the present invention, the conversion of acrolein to acrylic acid is from about 90 to 99 percent or greater and more preferably from about 95 to 99 percent or greater. Preferably, the overall conversion of producing acrylic acid from propylene over the two-stage operation in a per pass yield is not less than 70 mol %, preferably not less than 80 mol %.

The acrylic acid produced in the process of the present invention may be recovered by any means known to those skilled in the art, e.g., by absorption or fractionation, or further processes as disclosed in U.S. Pat No. 4,999,452.

The invention is hereafter described with reference to FIG. 1 and FIG. 2 which are not intended to limit the scope of the claims that follow.

Figure 1:
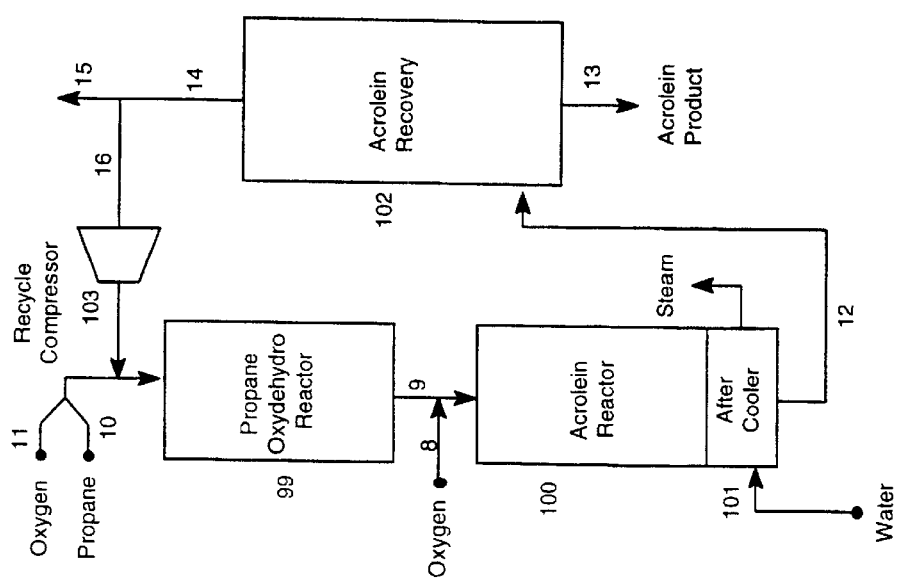
FIG. 1 is a simplified process flow diagram of a process for converting propane to acrolein in accordance with the present invention.

FIG. 1 represents the process configured to produce primarily acrolein. Small amounts of acrylic acid would also be made and could be recovered as a co-product, if desired. A gaseous propane feedstream 10 comprising 90 mol % propane and 10 mol % propylene and a gaseous oxygen feedstream 11 are fed to reactor 99, i.e., alkene reaction zone, containing a heterogeneous oxidative dehydrogenation catalyst, i.e., an alkene reaction catalyst, such as the preferred catalysts described herein. The oxygen feed may be pure, or an air feed may be used. Recycle stream 16 is also fed to reactor 99. Stream 16 contains unconverted propane and oxygen which passed through the process without conversion at an earlier time. Stream 16 also contains propylene and water and various noncondensable gases which are not reactive in the process. Non-reactive gases would include, but not be limited to, carbon dioxide and carbon monoxide, and for the air-based process, nitrogen. All feedstreams are preheated to approximately the operating temperature of reactor 99, which operates at between 300 and 400° C. The pressure of the feedstreams is slightly greater than the reactor pressure, which is between 15 and 60 psia. Reactor 99 is preferably operated at conversions which provide enhanced conversion to acrolein in reactor 100 (described below). Quite surprisingly, these conversions are lower than the highest conversions possible in the propane oxidation reactor. The gaseous species and the solid catalyst are contacted effectively in the reactor, which may have various designs including fixed or fluidized catalyst beds. The propane conversion to propylene is in the range of 10 to 40%. The gas product stream 9 contains the propylene product, unreacted propane and oxygen, water, small amounts by-products, and the nonreactive feed species.

The crude propylene product stream 9 is passed directly, without purification, to the propylene oxidation reactor 10, i.e., aldehyde reaction zone, where the contained propylene is oxidized to acrolein. Additional oxygen is fed to reactor 100 in stream 8. Reactor 100 contains a heterogeneous catalyst for the oxidation of propylene, i.e., aldehyde reaction catalyst, such as the preferred catalysts described herein. The gaseous reactant and solid catalyst are contacted effectively in the reactor, which may have various designs including fixed or fluidized catalyst beds. Reactor 100 operates in the temperature range of 300 to 400° C. and a pressure range of 15 to 50 psia. The conversion of the contained propylene is approximately 90%, but may be in the range of 70 to 100%. The principal product is acrolein with acrylic acid being a minor co-product. The effluent stream 12 is immediately cooled to approximately 250° C. in after cooler 101. Stream 12 has a pressure of approximately 20 psia, but it can range from 15 to 50 psia.

An additional advantage to the propane feedstock for acrolein production is the reduced temperature severity of the acrolein reactor. The higher heat capacity of propane, compared to conventional diluents such as nitrogen and steam, can reduce the hot spot temperature and moderate the temperature variation throughout the acrolein reactor. The lower temperature leads to reduced conversion to acrylic acid and carbon oxides and enhanced selectivity to acrolein.

A wide variety of recovery and refining schemes known to those skilled in the art, e.g., absorption and fractionation, may be employed to separate acrolein from effluent stream 12. A preferred feature of the separation scheme is that it avoid contamination of the gas stream with potential catalyst poisons. The presence of poisons for either the oxydehydrogenation catalyst or the acrolein catalyst would preclude direct recycle of the unreacted gases back to the reactor sequence. The recovered acrolein is removed from the separation unit in stream 13 and the unreacted gases leave the unit in stream 14. The temperature and pressure of stream 14 depend upon the specific acrolein separation process used, but will typically be in the range of 30 to 70° C. and 15 to 30 psia. Stream 14 is composed of propane, propylene, oxygen and various non reactive gases noted previously. Stream 14 is divided into recycle stream 16, which contains the majority of the flow, and the small purge stream 15. The magnitude of purge stream 15 is selected to prevent the slow accumulation of minor, but undesirable, reaction by-products. Stream 16 is compressed to a pressure slightly above the working pressure of reactor 99 and mixed with feedstreams 10 and 11.

FIG. 2 represents the process configured to produce acrylic acid by incorporating a third reactor positioned after the acrolein reactor. Operation of the oxydehydrogenation reactor 199 is the same as operation of reactor 99 in FIG. 1. Operation of the acrolein reactor 200 is very similar to the operation of reactor 100, with the possible exception that the temperature, pressure and/or oxygen content may be shifted modestly to favor the formation of acrylic acid over acrolein. Discharge stream 22 from reactor 200 is not cooled but rather is combined with additional oxygen from stream 23 to form feedstream 24, which enters acrylic acid reactor 201, i.e., carboxylic acid reaction zone.

Reactor 201 contains a heterogeneous catalyst for the conversion of acrolein to acrylic acid, i.e., carboxylic acid reaction catalyst, such as the preferred catalysts described herein. Reactor 201 is designed to contact effectively the catalyst and reactant gases. The conversion of acrolein to acrylic acid is high, in the range of 70 to 100%. The effluent gases are cooled in after cooler 202 and routed in stream 25 to acrylic acid recovery unit 203.

Many possible recovery schemes known to those skilled in the art are possible for separating acrylic acid from the residual reactants, gaseous by-products and diluent gases. As for the acrolein process shown in FIG. 1, a preferred feature of the separation scheme is that it avoid contamination of the gas stream with potential catalyst poisons. The presence of poisons for either the oxyhydrogenation catalyst or the acrolein/acrylic acid catalyst would preclude direct recycle of the unreacted gases back to the reactor sequence. The recovered acrylic acid is removed from the separation unit in stream 26 and the unreacted gases leave the unit in stream 27. The temperature and pressure of stream 27 depend upon the specific acrylic acid separation process used, but will typically be in the range of 30 to 70° C. and 15 to 30 psia. Stream 27 is composed of propane, propylene, oxygen and various nonreactive gases such as carbon monoxide, carbon dioxide, and, for an air-base process, nitrogen. Stream 27 is divided into recycle stream 29, which contains the majority of the flow, and the small purge stream 28. The magnitude of purge stream 28 is selected to prevent the slow accumulation of minor, but undesirable, reaction by-products. Stream 29 is compressed to a pressure slightly above the working pressure of reactor 199 and mixed with feedstreams 20 and 21.

EXAMPLES

The following examples are provided for illustrative purposes and are not intended to limit the scope of the claims which follow:

Example 1

This example shows the effect of utilizing propane to improve the efficiency of the reaction of propylene to acrolein. The experiments were carried out in a pilot-scale reactor system of two single reactor tubes of typical commercial dimensions. The first reactor tube contained a commercial propylene-to-acrolein catalyst which is comprised of bismuth, molybdenum, and iron oxides and other promoters. The second stage, which was close-coupled to the first, contained a commercial acrolein-to-acrylic acid catalyst comprised of bismuth, molybdenum, and iron oxides and other promoters. The second stage was used as an effective means of converting acrolein for disposal. Each stage had a jacket of a heat transfer fluid to remove heat of reaction. Thermocouples were placed strategically to measure hot spots in each system. The gaseous reactants were introduced via gas mass flow meters. The pressure at the entrance of the first stage was held at a constant 28 psig. The final product out of the second stage was passed through a scrubber and then condensed to equilibrium at 4° C., leaving only noncondensables. Concentration measurements of the feed, first-stage effluent, second-stage effluent, and the recycle stream were obtained via a gas chromatograph. Fresh propylene feed concentration was held at 8.2 mole percent and the gas hourly space velocity held at 1800 $hr^{-1}$.

Example 1-A

A baseline experiment was run with a 303° C. jacket temperature, 12.1 mole percent feed oxygen concentration, 49.3 mole percent feed nitrogen concentration, 30.0 mole percent steam concentration, and 0.3 mole percent feed propane concentration. Overall, the process was once-through only with no recycle. In the first stage, 90.5 percent of the feed propylene was consumed by the reaction. Of the propylene consumed, 79.9 percent went directly to forming acrolein in the first-stage outlet. Overall, 72.3 percent of the propylene fed to the system ends up as the useful product acrolein, while the rest is essentially lost. To make 3.8 standard liters per minute ("slm") of acrolein, 5.3 slm of propylene are required. This experiment is representative of typical commercial operation.

Example 1-B

In comparison, a recycle process was run with a high concentration of propane at similar conditions of active ingredients. The experiment was run with a jacket temperature of 303° C., 14.1 mole percent feed oxygen concentration, 8.7 mole percent feed water concentration, and 6.2 mole percent propane concentration. Essentially no nitrogen was in the feed. 98–99 percent of the second-stage noncondensable gases were returned to feed of the first stage to maintain constant pressure levels. In the first stage, 90.6 percent of the feed propylene was consumed by reaction. Of the propylene consumed, 87.6 percent went directly to forming acrolein in the first-stage outlet. Overall, 87.5 percent of the propylene fed to the system ends up as acrolein. To make 3.8 slm of acrolein, 4.4 slm of propylene is required. The experiment requires only 83 percent of the propylene required for once-through operation.

The improvement in propylene utilization arises from two factors. The first is the nearly complete recycling of unreacted material back to the front of the reactor. This accounts for 60 percent of the decrease in propylene requirements. The second factor is the presence of the relatively high concentration of propane in the feed. This increased concentration increases the flowing heat capacity and reduced temperatures in the system considerably. Overall, this effect accounts for 40 percent of the observed improvement in propylene usage.

Propane is introduced to the process as an impurity in the propylene feed. The propane levels of this experiment are consistent with 1–2 mole percent impurity level. Recycle operation makes economically viable the use of lower-purity propylene which can be more cost effective.

Although the invention has been described with respect to specific aspects, those skilled in the art will recognize that other aspects are intended to be within the scope of the claims that follow.

What is claimed is:

1. A process for producing an unsaturated carboxylic acid having up to about 5 carbon atoms per molecule comprising:
   (i) passing a feedstream comprising an alkane having up to about 5 carbon atoms per molecule, oxygen and a recycle gas comprising the alkane, an alkene having the same number of carbon atoms as said alkane, oxygen and at least one of carbon monoxide or carbon dioxide to an alkene reaction zone wherein the feedstream is contacted with an alkene reaction catalyst at conditions effective to promote the oxidation of the alkane by oxydehydrogenation to provide a first effluent stream comprising the alkene, unreacted alkane and water wherein:
      (a) the conversion of the alkane to the alkene is from about 5 to 40 percent and the selectivity of the conversion of the alkane to the alkene is from about 50 to 98 percent; and
      (b) said alkane and oxygen being present in a molar ratio of from 5 to 40 moles of the alkane per mole of oxygen;
   (ii) passing the first effluent stream to an aldehyde reaction zone wherein the first effluent stream is contacted with an aldehyde reaction catalyst at conditions effective to promote the conversion of the alkene to an aldehyde having the same number of carbon atoms as said alkene to provide a second effluent stream comprising the aldehyde, the alkene and the alkane;
   (iii) passing the second effluent stream to a carboxylic acid reaction zone wherein the second effluent stream is contacted with a carboxylic acid reaction catalyst at conditions effective to promote the conversion the conversion of the aldehyde to an unsaturated carboxylic acid having the same number of carbon atoms as said aldehyde to provide a third effluent stream comprising the alkene, the alkane, the unsaturated carboxylic acid and at least one of carbon monoxide or carbon dioxide;
   (iv) separating the third effluent stream into a liquid product stream comprising the carboxylic acid and a recycle gas stream comprising said recycle stream; and (v) recycling at least a portion of the recycle gas stream to the alkene reaction zone to comprise a portion of said feedstream;

characterized in that the alkene feedstream comprises an amount of alkane of from about 5 to 70 volume percent and effective to provide a alkene-to-aldehyde reaction efficiency of from about 75 to 90 mole percent.

2. The process of claim 1 wherein the concentration of the alkane in the first effluent stream is from about 5 to 70 mole percent of the alkane based on the total moles in the first effluent stream.

3. The process of claim 2 wherein the concentration of the alkane in the first effluent stream is from about 10 to 60 mole percent of the alkane based on the total moles in the first effluent stream.

4. The process of claim 1 wherein the alkane is butane, the aldehyde is methacrolein and the carboxylic acid is methacrylic acid.

5. A process for producing acrylic acid comprising:

(i) passing a feedstream comprising propane, oxygen and a recycle gas comprising propane, propylene, oxygen and at least one of carbon monoxide or carbon dioxide to a propylene reaction zone wherein the feedstream is contacted with a propane reaction catalyst at conditions effective to promote the oxidation of propane by oxydehydrogenation to provide a first effluent stream comprising propylene, unreacted propane and water, wherein:

(a) the conversion of propane to propylene is from about 5 to 40 percent and the selectivity of the conversion of propane to propylene from about 50 to 98 percent; and (b) said propane and oxygen being present in a molar ratio of from 5 to 40 moles of propane per mole of oxygen;

(ii) passing the first effluent stream to an acrolein reaction zone wherein the first effluent stream is contacted with an acrolein reaction catalyst at conditions effective to promote the conversion of propylene to acrolein to provide a second effluent stream comprising acrolein, propylene, propane and acrylic acid;

(iii) passing the second effluent stream to an acrylic acid reaction zone wherein the second effluent stream is contacted with an acrylic acid reaction catalyst at conditions effective to promote the conversion of acrolein to acrylic acid to provide a third effluent stream comprising propylene, propane, acrylic acid and at least one of carbon monoxide or carbon dioxide;

(iv) separating the third effluent stream into a liquid product stream comprising acrylic acid and a recycle gas stream comprising said recycle gas; and (v) recycling at least a portion of the recycle gas stream to the propylene reaction zone to comprise a portion of said feedstream;

characterized in that the propylene feedstream comprises an amount of propane of from about 5 to 70 volume percent and effective to provide a propylene-to-acrolein reaction efficiency of from about 75 to 90 mole percent.

6. The process of claim 5 wherein the concentration of propane in the first effluent stream is from about 5 to 70 mole percent of propane based on the total moles in the first effluent stream.

7. The process of claim 6 wherein the concentration of propane in the first effluent stream is from about 10 to 60 mole percent of propane based on the total moles in the first effluent stream.

8. The process of claim 5 wherein the propylene reaction zone and the acrolein reaction zone are combined in a single reactor.

9. The process of claim 8 wherein the propylene reaction catalyst and the acrolein reaction catalyst are commingled.

10. The process of claim 8 wherein the propylene reaction catalyst and the acrolein reaction catalyst are contained within separate zones within said reactor.

11. The process of claim 5 wherein the feedstream comprises at least 30 mole percent propane.

12. The process of claim 5 wherein the feedstream comprises at least 80 mole percent propane.

13. The process of claim 5 wherein the conversion of propylene is not less than 70 mole percent.

* * * * *